(12) United States Patent
Lee et al.

(10) Patent No.: US 9,744,243 B2
(45) Date of Patent: Aug. 29, 2017

(54) COMPOSITION OF EXTERNAL APPLICATION TO SKIN

(71) Applicant: NEOPHARM CO., LTD., Daejeon (KR)

(72) Inventors: Shin-Hee Lee, Daejeon (KR); Yoon Kim, Daejeon (KR); Su-Hwan Kim, Daejeon (KR); Byeong-Deog Park, Daejeon (KR)

(73) Assignee: NEOPHARM CO., LTD., Daejeon (KR)

( * ) Notice: Subject to any disclaimer, the term of this patent is extended or adjusted under 35 U.S.C. 154(b) by 56 days.

(21) Appl. No.: 14/647,395

(22) PCT Filed: Nov. 29, 2013

(86) PCT No.: PCT/KR2013/011019
§ 371 (c)(1),
(2) Date: Aug. 19, 2015

(87) PCT Pub. No.: WO2014/084670
PCT Pub. Date: Jun. 5, 2014

(65) Prior Publication Data
US 2015/0335756 A1    Nov. 26, 2015

(30) Foreign Application Priority Data

Nov. 29, 2012  (KR) .................. 10-2012-0137196
Nov. 28, 2013  (KR) .................. 10-2013-0145947

(51) Int. Cl.
| | | |
|---|---|---|
| A61K 8/02 | (2006.01) |
| A61K 47/44 | (2017.01) |
| A61K 47/10 | (2017.01) |
| A61K 47/18 | (2017.01) |
| A61K 9/00 | (2006.01) |
| A61K 9/107 | (2006.01) |
| A61K 8/36 | (2006.01) |
| A61K 8/37 | (2006.01) |
| A61K 8/39 | (2006.01) |
| A61K 8/55 | (2006.01) |
| A61K 8/63 | (2006.01) |
| A61K 8/68 | (2006.01) |
| A61Q 19/00 | (2006.01) |
| A61K 9/127 | (2006.01) |
| A61K 8/34 | (2006.01) |
| A61K 9/06 | (2006.01) |

(52) U.S. Cl.
CPC ............ *A61K 47/44* (2013.01); *A61K 8/0295* (2013.01); *A61K 8/342* (2013.01); *A61K 8/361* (2013.01); *A61K 8/375* (2013.01); *A61K 8/39* (2013.01); *A61K 8/553* (2013.01); *A61K 8/63* (2013.01); *A61K 8/68* (2013.01); *A61K 9/0014* (2013.01); *A61K 9/06* (2013.01); *A61K 9/107* (2013.01); *A61K 9/1274* (2013.01); *A61K 47/10* (2013.01); *A61K 47/18* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,916,578 A | 6/1999 | Kawada et al. | |
| 2005/0238677 A1 | 10/2005 | Mercier et al. | |
| 2014/0023600 A1* | 1/2014 | Fumagalli | A61K 8/737 424/59 |

FOREIGN PATENT DOCUMENTS

| | | |
|---|---|---|
| KR | 10-2000-0055082 A | 9/2000 |
| KR | 10-2002-0070154 A | 9/2002 |
| KR | 10-2007-0117800 A | 12/2007 |

* cited by examiner

*Primary Examiner* — Susan Tran
(74) *Attorney, Agent, or Firm* — Novick, Kim & Lee, PLLC; Jae Youn Kim

(57) ABSTRACT

The composition of external application to the skin according to the present invention may specifically control the relative amount between long-chain amides and sterols and the relative amount between lipid components and an emulsifier in the emulsion having a multi-layered lamella structure, the emulsion comprising a relatively larger content of dermatologically useful hydrophobic material in a formulation. Thus, the formulation having significantly high stability and excellent characteristics can be obtained in spite of the high content in the lipid components and the emulsifier.

7 Claims, No Drawings

COMPOSITION OF EXTERNAL APPLICATION TO SKIN

TECHNICAL FIELD

The present invention relates, in general, to a multi-lamellar emulsion type composition for skin external application, which comprises a combination of lipid components, including long-chain amide, sterol, fatty acid and fatty alcohol, an emulsifier and various oil components, and more particularly, to a multi-lamellar emulsion type composition for skin external application, which stably contains relatively large amounts of dermatologically useful oleophilic substances in the formulation thereof.

BACKGROUND ART

Generally, emulsion type compositions for skin external application contain an emulsifier in an amount of about 20 wt % based on the weight of oil. In addition, the compositions contain various skin conditioning agents, thickeners, preservatives, antioxidants, fragrances, etc. Because oil is highly effective in imparting moisturization to the skin, various efforts have been made to increase the content of oil in the compositions.

Methods that have been widely used to increase the content of oil in the prior art include a method of increasing the content of an emulsifier, and a method of increasing the content of a thickener. More specifically, in the method of increasing the content of an emulsifier, the content of an emulsifier functioning to prevent the separation between oil and water for a certain period of time is increased so that an increased amount of oil will be emulsified. In the method of increasing the content of a thickener, the viscosity of an emulsion is increased to prevent emulsion particles from moving by external environments such as temperature and heat, so that the formulation of the emulsion can be stably maintained for a long period of time while it contains a large amount of oil. The method that increases the emulsifier content enables easy emulsification, but has a shortcoming in that the emulsifier can cause skin irritation. On the other hand, the method that increases the thickener content has a disadvantage in that the emulsion is difficult to contain a large amount of oil, compared to the method that increases the emulsifier content, but has an advantage in that the emulsion is stably maintained for a long period of time.

When emulsification occurs, emulsion layers formed between the oil phase and the water phase are self-assembled by the geometrical structure of components thereof and the interaction between functional groups present in the molecules so as to minimize energy. Such self-assembly structures include micellar, hexagonal, cubic, lamellar, inverse cubic, inverse hexagonal and inverse micellar structures. Among them, the lamellar structure having a repeated multi-layer structure has an advantage, particularly in terms of stability, and is a skin-friendly structure that can be found in lipids between human keratinocytes. The lipid components that are used herein have no emulsifying function by themselves, but assist in the formation of lamellar self-assembly structures and increase the stability of formed emulsion layers.

In conclusion, it can also be contemplated to obtain a stable emulsion using lipid components other than emulsifiers or thickeners. The lipid components discussed herein have weak amphiphilic properties and are considered to have properties intermediate between the properties of surfactants and the properties of oil.

Thus, in the case of various multi-lamellar emulsions according to the prior art, stable compositions for skin external application are prepared using these emulsions in combination with lipid components that make the emulsion structures stable. However, in all these compositions, the content of lipid components, including long-chain amide, sterol, fatty acid and fatty alcohol, in the formulation, is generally 4 wt % or less, or at most 6 wt %, or 7.5 wt % or less even in specific cases, and the content of long-chain amide and sterol is also generally 1.3 wt % or less, or about 2.0 wt % even in specific cases.

Formulations containing about 15 wt % or more, particularly 15 wt % or more, of the lipid components, and about 3-4 wt % of long-chain amide and sterol, have advantages in that these are easy to transport for export or the like or store, are easily processed into final products, and can also be used as final products in some cases. Despite such advantages, there is a problem in that it is very difficult to form a stable multi-lamellar structure in conventional formulations.

DISCLOSURE

Technical Problem

Therefore, it is an object of the present invention to provide a multi-lamellar emulsion type composition for skin external application, which contains relatively large amounts of dermatologically useful oleophilic substances in the formulation thereof and can be stably maintained in an emulsion state over a long period of time.

Technical Solution

In order to accomplish the above object, the present invention provides a multi-lamellar emulsion type composition for skin external application, which comprises: 15-22 wt % of lipid components comprising, based on the total weight of the composition, 3-4 wt % of long-chain amide and sterol and 12-18 wt % of fatty acid and fatty alcohol; 6-10 wt % of an emulsifier; 12-18 wt % of oil; and a balance of purified water, wherein the ratio of the content of the long-chain amide to that of the sterol is 0.1-1.8:1 by weight, the ratio of the content of the lipid components to the emulsifier is 1.8-3.0:1 by weight, and the sum of the contents of the lipid components and the emulsifier is 21-32 wt % based on the total weight of the composition.

Advantageous Effects

A composition for skin external application according to the present invention is an emulsion formulation containing relatively large amounts of long-chain amide and sterol that are dermatologically useful substances. According to the present invention, both the ratio of the lipid components to the emulsifier and the ratio of long-chain amide to sterol are controlled to specific ratios, and, as a result, the composition of the present invention has high phase stability with time, excellent properties, a good feeling, and excellent applicability to various formulations.

BEST MODE

Hereinafter, the present invention will be described in detail.

A composition for skin external application according to the present invention is a multi-lamellar emulsion comprising: lipid compounds comprising long-chain amide, sterol, fatty acid and fatty alcohol; an emulsifier; oil; purified water; a thickener; and polyhydric alcohol.

Typical examples of the long-chain amide that is used in the present invention may include ceramides that are found in the skin. Ceramides are known to be very important in moisturization and skin protection and are synthesized to have a structure identical or similar to that found in the human body. The ceramide that is used in the present invention may be selected from among ceramide analogues, including myristoyl oxostearamide MEA, myristoyl oxoarachamide MEA, palmitoyl oxostearamide MEA, palmitoyl oxoarachamide MEA, PC-9S (Neopharm Co., Ltd., Korea) consisting of a mixture of these four compounds, and dihydroxyisopropyl palmoylpalmamide, and natural ceramides, including ceramide-1, ceramide-2, ceramide-3, ceramide-3B, ceramide-4, ceramide-5, and ceramide-6. These ceramides may be used alone or in a mixture of two or more.

The sterol that is used in the present invention may be any one or a mixture of two or more selected from among cholesterol and its derivatives, including cholesteryl sulfate, cholesteryl acetate, cholesteryl stearate, cholesteryl isostearate, and cholesteryl hydroxystearate, and plant-derived phytosterol. Among them, phytosterol or a mixture of phytosterol and cholesterol is preferable in terms of maintaining phase stability.

In addition, the fatty acid that is used in the present invention is palmitic acid, stearic acid, arachidic acid, or a mixture of two or more thereof. A fatty acid having a short carbon chain length or containing several multiple bonds is not preferable, because it can weaken the resulting multi-lamellar structure.

The fatty alcohol that is used in the present invention may be cetyl alcohol, stearyl alcohol, cetearyl alcohol, behenyl alcohol, or a mixture of two or more thereof. A fatty alcohol having a short carbon chain length or containing several multiple bonds is not preferable, because it can weaken the resulting multi-lamellar structure. In the present invention, fatty acids may be used alone or in a mixture, and fatty alcohols may also be used alone or in a mixture.

Meanwhile, the emulsifier that is used in the present invention is an emulsifier suitable for forming a multi-lamellar emulsion structure. Specifically, the emulsifier that is used in the present invention may be selected from among polyglycerins, including polyglyceryl-10 dipalmitate, polyglyceryl-10 distearate, polyglyceryl-10 stearate, and polyglyceryl-10 oleate; sugar esters, including sorbitan palmitate, sorbitan stearate, sorbitan isostearate, sorbitan sesquistearate, sorbitan oleate, sorbitan sesquioleate, sorbitan olivate, and sucrose cocoate; glyceryl esters, including glyceryl stearate and glyceryl oleate; and hydrogenated emulsifiers, including hydrogenated lecithin and hydrogenated palm glyceride. Among these emulsifiers, at least two emulsifiers selected from among polyglyceryl-10 distearate, hydrogenated lecithin, glyceryl stearate and sorbitan stearate are preferably used in order to a suitable HLB value in view of other components.

In addition, examples of a polyhydric alcohol that may be used in the present invention include glycerin, 1,2-propanediol, 1,3-propanediol, 1,3-butanediol, 1,2-pentanediol, etc., and examples of a thickener that may be used in the present invention include carbomer, xanthan gum, and celluloses. However, these may be suitably selected according to circumstances.

Meanwhile, the oil that is used in the emulsion of the present invention may be suitably selected according to circumstances. Dermatologically useful substances that that may be contained in emulsion particles are preferably oleophilic substances, because the emulsion is an oil-in-water type emulsion. Specifically, the dermatologically useful substances may include various oleophilic vegetable oils, liquid paraffin, paraffin wax, squalane, and caprylic/capric triglyceride.

In the multi-lamellar emulsion type composition for skin external application according to the present invention, long-chain amide and sterol that are dermatologically useful lipid components are contained in a relatively large amount of 3-4 wt %. In order to stabilize these lipid components, other lipid components including fatty acid and fatty alcohol are contained in a very large amount of 12-18 wt %. Thus, the composition for skin external application according to the present invention contain lipid components in an amount of 15-22 wt % based on the total weight of the composition.

On the other hand, the emulsifier is contained in a relatively small amount of 6-10 wt % based on the total weight of the composition, and the ratio of the content of the lipid components to that of the emulsifier is in the range of 1.8-3.0 by weight. Generally, it is known that, if the ratio of content of the lipid components to that of the emulsifier is more than 1.5:1 by weight, phase stability will be problematic. However, if the ratio of the content of the lipid components to that of the emulsifier in the composition of the present invention that contains the lipid components in a large amount of 15-22 wt % is about 0.6-1.5:1 by weight, there will be a problem in that the feeling of the formulation will be significantly reduced, and if the ratio of the content is more than 3.0:1 by weight, there will be a problem in that the stability of the formulation will be reduced due to precipitation resulting from a change in temperature.

Meanwhile, in the emulsion type composition for skin external application according to the present invention, the sum of the content of the lipid components functioning to maintain the stability of the emulsion plus the content of the emulsifier preferably in the range of 21-32 wt % based on the total weight of the composition. If this sum of the contents is less than 21 wt %, the desired emulsifying effect will be insufficient, and if it is more than 32 wt %, difficulty in ensuring the phase stability of the composition will increase, and the use of other components will be restricted, making it difficult to prepare formulations having various feelings.

In addition, through many experiments, the present inventors have empirically found that, when the composition for skin external application according to the present invention contains long-chain amide and sterol at a ratio of 0.1-1.8:1 by weight, this content ratio considerably contributes to the phase stability of the composition. If the content of sterol is reduced so that the content ratio will be more than 1.8, the phase stability will be reduced, and if the content ratio is less than 0.1, the content of the dermatologically useful substances will be excessively reduced. When sterol having a fused ring structure is used within the above content ratio, it contributes to maintaining the multi-lamellar emulsion of the present invention.

MODE FOR INVENTION

Hereinafter, the present invention will be described in detail with reference to examples and comparative examples. It is to be understood, however, that these examples are for illustrative purposes and are not intended to limit the scope of the present invention.

Examples 1 to 12 and Comparative Examples 1 to 12

According to the compositions shown in Tables 1 to 3 below, long-chain amide, sterol, fatty acid, fatty alcohol, a nonionic surfactant, a thickener and purified water were mixed with one another to prepare liquid crystal emulsions. The long-chain amide used was PC-9S (Neopharm Co., Ltd., Korea) consisting of a mixture of myristoyl/palmitoyl oxostearamide/arachamide MEA.

TABLE 1

| Components | Example 1 | Example 2 | Example 3 | Example 4 | Example 5 | Example 6 | Example 7 | Example 8 |
|---|---|---|---|---|---|---|---|---|
| Pseudoceramide | 1.0 | 1.5 | 2.0 | 2.5 | 1.0 | 1.5 | 2.0 | 2.5 |
| Polyglyceryl-10 distearate | 5.0 | 5.0 | 5.0 | 5.0 | | | | |
| Sorbitan stearate | | | | | 5.0 | 5.0 | 5.0 | 5.0 |
| Hydrogenated lecithin | | | | | | | | |
| Glyceryl stearate | 4.5 | 4.5 | 4.5 | 4.5 | 4.5 | 4.5 | 4.5 | 4.5 |
| Stearic acid | 4.5 | 4.5 | 4.5 | 4.5 | 4.5 | 4.5 | 4.5 | 4.5 |
| Cetearyl alcohol | 10.5 | 10.5 | 10.5 | 10.5 | 10.5 | 10.5 | 10.5 | 10.5 |
| Cholesterol | 0.6 | 0.6 | 0.4 | 0.4 | 0.6 | 0.6 | 0.4 | 0.4 |
| Phytosterol | 1.5 | 1.5 | 1.0 | 1.0 | 1.5 | 1.5 | 1.0 | 1.0 |
| Xanthan gum | q.s. | q.s. | q.s. | q.s. | q.s. | q.s. | q.s. | q.s. |
| Caprylic/capric triglyceride | 15.0 | 15.0 | 15.0 | 15.0 | 15.0 | 15.0 | 15.0 | 15.0 |
| Purified water | Balance | Balance | Balance | Balance | Balance | Balance | Balance | Balance |

TABLE 2

| Components | Example 9 | Example 10 | Example 11 | Example 12 |
|---|---|---|---|---|
| Pseudoceramide | 1.0 | 1.5 | 2.0 | 2.5 |
| Polyglyceryl-10 distearate | | | | |
| Sorbitan stearate | | | | |
| Hydrogenated lecithin | 2.0 | 2.0 | 2.0 | 2.0 |
| Glyceryl stearate | 4.5 | 4.5 | 4.5 | 4.5 |
| Stearic acid | 4.5 | 4.5 | 4.5 | 4.5 |
| Cetearyl alcohol | 10.5 | 10.5 | 10.5 | 10.5 |
| Cholesterol | 0.6 | 0.6 | 0.4 | 0.4 |
| Phytosterol | 1.5 | 1.5 | 1.0 | 1.0 |
| Xanthan gum | q.s. | q.s. | q.s. | q.s. |
| Caprylic/capric triglyceride | 15.0 | 15.0 | 15.0 | 15.0 |
| Purified water | Balance | Balance | Balance | Balance |

TABLE 3

| Components | Comp. Example 1 | Comp. Example 2 | Comp. Example 3 | Comp. Example 4 | Comp. Example 5 | Comp. Example 6 |
|---|---|---|---|---|---|---|
| Pseudoceramide | 0.5 | 3.0 | 0.5 | 3.0 | 0.5 | 3.0 |
| Polyglyceryl-10 distearate | 5.0 | 5.0 | | | | |
| Sorbitan stearate | | | 5.0 | 5.0 | | |
| Hydrogenated lecithin | | | | | 5.0 | 5.0 |
| Glyceryl stearate | 4.5 | 4.5 | 4.5 | 4.5 | | |
| Stearic acid | 4.5 | 4.5 | 4.5 | 4.5 | 4.5 | 4.5 |
| Cetearyl alcohol | 10.5 | 10.5 | 10.5 | 10.5 | 10.5 | 10.5 |
| Cholesterol | | | | | | |
| Phytosterol | | | | | | |
| Xanthan gum | q.s. | q.s. | q.s. | q.s. | q.s. | q.s. |
| Caprylic/capric triglyceride | 15.0 | 15.0 | 15.0 | 15.0 | 15.0 | 15.0 |
| Purified water | Balance | Balance | Balance | Balance | Balance | Balance |

TABLE 4

| Components | Comp. Example 7 | Comp. Example 8 | Comp. Example 9 | Comp. Example 10 | Comp. Example 11 | Comp. Example 12 |
|---|---|---|---|---|---|---|
| Pseudoceramide | 0.5 | 3.0 | 0.5 | 3.0 | 0.5 | 3.0 |
| Polyglyceryl-10 distearate | 5.0 | 5.0 | | | | |
| Sorbitan stearate | | | 5.0 | 5.0 | | |
| Hydrogenated lecithin | | | | | 5.0 | 5.0 |
| Glyceryl stearate | 4.5 | 4.5 | 4.5 | 4.5 | | |
| Stearic acid | 4.5 | 4.5 | 4.5 | 4.5 | 4.5 | 4.5 |
| Cetearyl alcohol | 10.5 | 10.5 | 10.5 | 10.5 | 10.5 | 10.5 |
| Cholesterol | 7.0 | 8.0 | 0.5 | 6.0 | 2.0 | 0.5 |
| Phytosterol | | | | | | |

TABLE 4-continued

| Components | Comp. Example 7 | Comp. Example 8 | Comp. Example 9 | Comp. Example 10 | Comp. Example 11 | Comp. Example 12 |
|---|---|---|---|---|---|---|
| Xanthan gum | q.s. | q.s. | q.s. | q.s. | q.s. | q.s. |
| Caprylic/capric triglyceride | 15.0 | 15.0 | 15.0 | 15.0 | 15.0 | 15.0 |
| Purified water | Balance | Balance | Balance | Balance | Balance | Balance |

Examples 13 to 48

Formulation

According to the compositions shown in Tables 5 to 9 below, long-chain amide, sterol, fatty acid, fatty alcohol, a nonionic surfactant, a thickener and purified water were mixed with one another to prepare liquid crystal emulsions. The long-chain amide used was either PC-9S (Neopharm Co., Ltd., Korea) consisting of a mixture of myristoyl/palmitoyl oxostearamide/arachamide MEA, or one selected from among ceramide-3 and ceramide-3B as natural ceramides.

TABLE 5

| Components | Example 13 | Example 14 | Example 15 | Example 16 | Example 17 | Example 18 | Example 19 | Example 20 |
|---|---|---|---|---|---|---|---|---|
| Pseudoceramide (PC-9S) | 1.8 | 1.8 | | | 1.2 | 1.2 | 1.2 | 1.2 |
| Pseudoceramide (PC-5) | | | 1.8 | 1.8 | | | | |
| Ceramide 3 | | | | | 0.1 | 0.1 | | |
| Ceramide 3B | | | | | | | 0.1 | 0.1 |
| Polyglyceryl-10 distearate | 5.0 | 5.0 | 5.0 | 5.0 | 5.0 | 5.0 | 5.0 | 5.0 |
| Sorbitan stearate | | | | | | | | |
| Hydrogenated lecithin | | | | | | | | |
| Glyceryl stearate | 4.5 | 4.5 | 4.5 | 4.5 | 4.5 | 4.5 | 4.5 | 4.5 |
| Stearic acid | 4.5 | 4.5 | 4.5 | 4.5 | 4.5 | 4.5 | 4.5 | 4.5 |
| Cetearyl alcohol | 10.5 | 10.5 | 10.5 | 10.5 | 10.5 | 10.5 | 10.5 | 10.5 |
| Cholesterol | 0.6 | | 0.6 | | 0.6 | | 0.6 | |
| Phytosterol | 1.5 | 2.0 | 1.5 | 2.0 | 1.5 | 2.0 | 1.5 | 2.0 |
| Xanthan gum | q.s. | q.s. | q.s. | q.s. | q.s. | q.s. | q.s. | q.s. |
| Caprylic/capric triglyceride | 15.0 | 15.0 | 15.0 | 15.0 | 15.0 | 15.0 | 15.0 | 15.0 |
| Purified water | Balance | Balance | Balance | Balance | Balance | Balance | Balance | Balance |

TABLE 6

| Components | Example 21 | Example 22 | Example 23 | Example 24 | Example 25 | Example 26 | Example 27 | Example 28 |
|---|---|---|---|---|---|---|---|---|
| Pseudoceramide (PC-9S) | 1.2 | 1.2 | 1.2 | 1.2 | 1.8 | 1.8 | | |
| Pseudoceramide (PC-5) | | | | | | | 1.8 | 1.8 |
| Ceramide 3 | 0.1 | 0.1 | | | | | | |
| Ceramide 3B | | | 0.1 | 0.1 | | | | |
| Polyglyceryl-10 distearate | 5.0 | 5.0 | 5.0 | 5.0 | | | | |
| Sorbitan stearate | | | | | 5.0 | 5.0 | 5.0 | 5.0 |
| Hydrogenated lecithin | | | | | | | | |
| Glyceryl stearate | 4.5 | 4.5 | 4.5 | 4.5 | 4.5 | 4.5 | 4.5 | 4.5 |
| Stearic acid | 4.5 | 4.5 | 4.5 | 4.5 | 4.5 | 4.5 | 4.5 | 4.5 |
| Cetearyl alcohol | 10.5 | 10.5 | 10.5 | 10.5 | 10.5 | 10.5 | 10.5 | 10.5 |
| Cholesterol | 0.6 | | 0.6 | | 0.6 | | 0.6 | |
| Phytosterol | 1.5 | 2.0 | 1.5 | 2.0 | 1.5 | 2.0 | 1.5 | 2.0 |
| Xanthan gum | q.s. | q.s. | q.s. | q.s. | q.s. | q.s. | q.s. | q.s. |
| Caprylic/capric triglyceride | 15.0 | 15.0 | 15.0 | 15.0 | 15.0 | 15.0 | 15.0 | 15.0 |
| Purified water | Balance | Balance | Balance | Balance | Balance | Balance | Balance | Balance |

TABLE 7

| Components | Example 29 | Example 30 | Example 31 | Example 32 | Example 33 | Example 34 | Example 35 | Example 36 |
|---|---|---|---|---|---|---|---|---|
| Pseudoceramide (PC-9S) | 1.2 | 1.2 | 1.2 | 1.2 | 1.2 | 1.2 | 1.2 | 1.2 |
| Pseudoceramide (PC-5) | | | | | | | | |
| Ceramide 3 | 0.1 | 0.1 | | | 0.1 | 0.1 | | |
| Ceramide 3B | | | 0.1 | 0.1 | | | 0.1 | 0.1 |
| Polyglyceryl-10 distearate | | | | | | | | |
| Sorbitan stearate | 5.0 | 5.0 | 5.0 | 5.0 | 5.0 | 5.0 | 5.0 | 5.0 |
| Hydrogenated lecithin | | | | | | | | |
| Glyceryl stearate | 4.5 | 4.5 | 4.5 | 4.5 | 4.5 | 4.5 | 4.5 | 4.5 |
| Stearic acid | 4.5 | 4.5 | 4.5 | 4.5 | 4.5 | 4.5 | 4.5 | 4.5 |
| Cetearyl alcohol | 10.5 | 10.5 | 10.5 | 10.5 | 10.5 | 10.5 | 10.5 | 10.5 |
| Cholesterol | 0.6 | | 0.6 | | 0.6 | | 0.6 | |
| Phytosterol | 1.5 | 2.0 | 1.5 | 2.0 | 1.5 | 2.0 | 1.5 | 2.0 |
| Xanthan gum | q.s. | q.s. | q.s. | q.s. | q.s. | q.s. | q.s. | q.s. |
| Caprylic/capric triglyceride | 15.0 | 15.0 | 15.0 | 15.0 | 15.0 | 15.0 | 15.0 | 15.0 |
| Purified water | Balance | Balance | Balance | Balance | Balance | Balance | Balance | Balance |

TABLE 8

| Components | Example 37 | Example 38 | Example 39 | Example 40 | Example 41 | Example 42 | Example 43 | Example 44 |
|---|---|---|---|---|---|---|---|---|
| Pseudoceramide (PC-9S) | 1.8 | 1.8 | | | 1.2 | 1.2 | 1.2 | 1.2 |
| Pseudoceramide (PC-5) | | | 1.8 | 1.8 | | | | |
| Ceramide 3 | | | | | 0.1 | 0.1 | | |
| Ceramide 3B | | | | | | | 0.1 | 0.1 |
| Polyglyceryl-10 distearate | | | | | | | | |
| Sorbitan stearate | | | | | | | | |
| Hydrogenated lecithin | 2.0 | 2.0 | 2.0 | 2.0 | 2.0 | 2.0 | 2.0 | 2.0 |
| Glyceryl stearate | 7.0 | 7.0 | 7.0 | 7.0 | 7.0 | 7.0 | 7.0 | 7.0 |
| Stearic acid | 4.5 | 4.5 | 4.5 | 4.5 | 4.5 | 4.5 | 4.5 | 4.5 |
| Cetearyl alcohol | 10.5 | 10.5 | 10.5 | 10.5 | 10.5 | 10.5 | 10.5 | 10.5 |
| Cholesterol | 0.6 | | 0.6 | | 0.6 | | 0.6 | |
| Phytosterol | 1.5 | 2.0 | 1.5 | 2.0 | 1.5 | 2.0 | 1.5 | 2.0 |
| Xanthan gum | q.s. | q.s. | q.s. | q.s. | q.s. | q.s. | q.s. | q.s. |
| Caprylic/capric triglyceride | 15.0 | 15.0 | 15.0 | 15.0 | 15.0 | 15.0 | 15.0 | 15.0 |
| Purified water | Balance | Balance | Balance | Balance | Balance | Balance | Balance | Balance |

TABLE 9

| Components | Example 45 | Example 46 | Example 47 | Example 48 |
|---|---|---|---|---|
| Pseudoceramide (PC-9S) | 1.2 | 1.2 | 1.2 | 1.2 |
| Pseudoceramide (PC-5) | | | | |
| Ceramide 3 | 0.1 | 0.1 | | |
| Ceramide 3B | | | 0.1 | 0.1 |
| Polyglyceryl-10 distearate | | | | |
| Sorbitan stearate | | | | |
| Hydrogenated lecithin | 2.0 | 2.0 | 2.0 | 2.0 |
| Glyceryl stearate | 7.0 | 7.0 | 7.0 | 7.0 |
| Stearic acid | 4.5 | 4.5 | 4.5 | 4.5 |
| Cetearyl alcohol | 10.5 | 10.5 | 10.5 | 10.5 |
| Cholesterol | 0.6 | | 0.6 | |
| Phytosterol | 1.5 | 2.0 | 1.5 | 2.0 |
| Xanthan gum | q.s. | q.s. | q.s. | q.s. |
| Caprylic/capric triglyceride | 15.0 | 15.0 | 15.0 | 15.0 |
| Purified water | Balance | Balance | Balance | Balance |

Experimental Example 1

Observation of Liquid Crystal Structure Using Polarizing Microscope

In order to confirm whether the emulsions prepared in the above Examples formed a liquid crystal, a characteristic Maltese cross appearing in the liquid crystal emulsions was observed. The results of the observation are shown in Table 10 below. To observe the Maltese cross, a polarizing microscope (Optiphto-2, Nikon) was used.

A suitable amount of each of the prepared emulsions was placed on a slide glass, covered with a cover glass, lightly pressed and then observed at 500× magnification.

Criteria for evaluation of formed liquid crystal structure:

1: excellent—the frequency or shape of the liquid crystal phase is normal;

2: good—the frequency of the liquid crystal phase is lower than the normal state, or a structure having a defective shape appears;

3: inadequate—the frequency of the liquid crystal phase is lower than the normal state, or a number of structures having a defective shape appear;

4: poor—little or no formation of the liquid crystal phase.

TABLE 10

Results of evaluation of polarizing microscope photographs of formulations

| Sample | Evaluation result |
| --- | --- |
| Example 1 | 1 |
| Example 4 | 1 |
| Example 7 | 1 |
| Example 9 | 1 |
| Example 10 | 1 |
| Example 11 | 1 |
| Example 13 | 1 |
| Example 15 | 1 |
| Example 21 | 1 |
| Example 24 | 1 |
| Example 25 | 1 |
| Example 32 | 1 |
| Example 37 | 1 |
| Example 38 | 1 |
| Example 40 | 1 |
| Example 41 | 1 |
| Example 45 | 1 |
| Example 48 | 1 |
| Comp. Example 1 | 3 |
| Comp. Example 2 | 2 |
| Comp. Example 3 | 3 |
| Comp. Example 4 | 2 |
| Comp. Example 5 | 3 |
| Comp. Example 6 | 2 |
| Comp. Example 7 | 2 |
| Comp. Example 8 | 1 |
| Comp. Example 9 | 2 |
| Comp. Example 10 | 2 |
| Comp. Example 11 | 2 |
| Comp. Example 12 | 2 |

As can be seen from the results in Table 10 above, in the case of all the Examples in which the ratio of the content of long-chain amide to that of sterol was 0.1-1.8:1 by weight, the ratio of the content of lipid to that of the emulsifier was 1.8-3.0:1 by weight, and the sum of the contents of lipid and the emulsifier was 21-32 wt %, it was shown that a good lamellar liquid crystal structure was formed. However, in the case of the Comparative Examples that do not satisfy the above conditions, the formation of emulsion particles was poor.

Experimental Example 2

Stability of Formulation

The stabilities of the emulsion formulations having a lamellar structure, prepared in the Examples of the present invention and the Comparative Examples, were measured in the following manner. The following samples were measured for the degree of separation and the degree of discoloration: samples obtained by placing the formulations of the Examples and Comparative Examples (described in Tables 11 to 13 below) in opaque glass containers and storing them in an incubator for 12 weeks; samples obtained by placing the formulations in opaque glass containers and storing them in a light-shielded refrigerator at 4° C. for 12 weeks; and samples obtained by storing the formulations in a temperature cycling chamber (from 5° C. to 45° C.) for 4 weeks. The degree of formulation separation and discoloration was evaluated on a six-point scale as follows, and the results of the evaluation are shown in Tables 5 and 6 below.

Criteria for evaluation of formulation separation and discoloration:

0: no change;

1: very slight separation (discoloration);

2: slight separation (discoloration);

3: slightly severe separation or precipitation (discoloration);

4: severe separation or precipitation (discoloration);

3: very severe separation or precipitation (discoloration).

TABLE 11

| Temperature | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| 45° C. | 0 | 0 | 0 | 0 | 0 | 0 | 0 | 0 | 0 | 0 | 0 | 0 |
| 4° C. | 0 | 0 | 0 | 0 | 0 | 0 | 0 | 0 | 0 | 0 | 0 | 0 |
| Cycling | 0 | 0 | 0 | 0 | 0 | 0 | 0 | 0 | 0 | 0 | 0 | 0 |

TABLE 12

| Temperature | Ex. 14 | Ex. 18 | Ex. 21 | Ex. 25 | Ex. 27 | Ex. 30 | Ex. 32 | Ex. 34 | Ex. 37 | Ex. 40 | Ex. 42 | Ex. 47 |
|---|---|---|---|---|---|---|---|---|---|---|---|---|
| 45° C. | 0 | 0 | 0 | 0 | 0 | 0 | 0 | 0 | 0 | 0 | 0 | 0 |
| 4° C. | 0 | 0 | 0 | 0 | 0 | 0 | 0 | 0 | 0 | 0 | 0 | 0 |
| Cycling | 0 | 0 | 0 | 0 | 0 | 0 | 0 | 0 | 0 | 0 | 0 | 0 |

TABLE 13

| Temperature | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 |
|---|---|---|---|---|---|---|---|---|---|---|---|---|
| 45° C. | 4 | 2 | 4 | 1 | 3 | 1 | 1 | 2 | 1 | 2 | 1 | 2 |
| 4° C. | 2 | 4 | 1 | 4 | 0 | 3 | 0 | 1 | 0 | 2 | 0 | 0 |
| Cycling | 4 | 2 | 3 | 1 | 4 | 0 | 1 | 2 | 1 | 3 | 1 | 2 |

As can be seen from the results in Tables 11 to 13 above, in the case of all the Examples in which the ratio of the content of long-chain amide to that of sterol was 0.1-1.8:1 by weight, the ratio of the content of lipid to that of the emulsifier was 1.8-3.0:1 by weight, and the sum of the contents of lipid and the emulsifier was 21-32 wt %, it was shown that the formulation were all stable at 45° C., 4° C. and the cycling temperature (from 45° C. to 5° C.), even though the dermatologically useful substances and the lipid components were contained in large amounts.

However, in the case of the Comparative Examples that do not satisfy all the above conditions, formulation separation occurred at 45° C., 4° C. and the cycling temperature (from 45° C. to 5° C.) (Comparative Examples 7 to 9), or particle precipitation appeared (Comparative Examples 8 and 10 to 12). This is believed to be because the pseudo-ceramide having a high melting point was contained in a large amount to reduce the content of the lipid component to thereby make the formulation unstable.

INDUSTRIAL APPLICABILITY

As described above, according to the present invention, the ratio of the content of lipid to that of the emulsifier is controlled to the above-specified ratio by reducing the content of the emulsifier, and the ratio of the content of long-chain amide to that of sterol is also controlled to the above-specified ratio. By doing so, a very stable formulation having excellent properties can be obtained, which has high contents of the lipid components and the emulsifier.

The invention claimed is:

1. A multi-lamellar emulsion composition for skin external application, which comprises:
   15-22 wt % of lipid components comprising, based on the total weight of the composition, 3-4 wt % of long-chain amide and sterol and 12-18 wt % of fatty acid and fatty alcohol;
   6-10 wt % of an emulsifier based on the total weight of the composition;
   12-18 wt % of oil based on the total weight of the composition; and
   a balance of purified water,
   wherein the ratio of the content of the long-chain amide to that of the sterol is 0.1-1.8:1 by weight, the ratio of the content of the lipid components to the emulsifier is 1.8-3.0:1 by weight, and the sum of the contents of the lipid components and the emulsifier is 21-32 wt % based on the total weight of the composition.

2. The composition of claim 1, wherein the long-chain amide is at least one compound selected from the group consisting of myristoyl oxostearamide MEA, myristoyl oxoarachamide MEA, palmitoyl oxostearamide MEA, palmitoyl oxoarachamide MEA, dihydroxyisopropyl palmoylpalmamide, ceramide-1, ceramide-2, ceramide-3, ceramide-3B, ceramide-4, ceramide-5, and ceramide-6.

3. The composition of claim 1, wherein the sterol is at least one compound selected from the group consisting of cholesterol, cholesteryl sulfate, cholesteryl acetate, cholesteryl stearate, cholesteryl isostearate, cholesteryl hydroxystearate, and phytosterol.

4. The composition of claim 3, wherein the sterol is phytosterol or a combination of phytosterol and cholesterol.

5. The composition of claim 1, wherein the emulsifier is at least one compound selected from the group consisting of polyglycerins, including polyglyceryl-10 dipalmitate, polyglyceryl-10 distearate, polyglyceryl-10 stearate, and polyglyceryl-10 oleate; sugar esters, including sorbitan palmitate, sorbitan stearate, sorbitan isostearate, sorbitan sesquistearate, sorbitan oleate, sorbitan sesquioleate, sorbitan olivate, and sucrose cocoate; glyceryl esters, including glyceryl stearate and glyceryl oleate; and hydrogenated emulsifiers, including hydrogenated lecithin and hydrogenated palm glyceride.

6. The composition of claim 5, wherein the emulsifier is a mixture of two or more selected from the group consisting of polyglyceryl-10 distearate, hydrogenated lecithin, glyceryl stearate, and sorbitan stearate.

7. The composition of claim 1, wherein the fatty acid is palmitic acid, stearic acid, arachidic acid, or a mixture of two or more thereof, and the fatty alcohol is cetyl alcohol, stearyl alcohol, cetearyl alcohol, behenyl alcohol, or a mixture of two or more thereof.

* * * * *